(12) United States Patent
Busoni

(10) Patent No.: US 12,702,851 B2
(45) Date of Patent: Aug. 11, 2026

(54) DISPOSABLE PROTECTION SYSTEM FOR CAPACITIVE RADIOFREQUENCY DELIVERY DEVICES

(71) Applicant: Maurizio Busoni, Florence (IT)

(72) Inventor: Maurizio Busoni, Florence (IT)

( * ) Notice: Subject to any disclaimer, the term of this patent is extended or adjusted under 35 U.S.C. 154(b) by 349 days.

(21) Appl. No.: 18/032,917

(22) PCT Filed: Oct. 27, 2021

(86) PCT No.: PCT/IB2021/059923

§ 371 (c)(1),
(2) Date: Apr. 20, 2023

(87) PCT Pub. No.: WO2022/090954

PCT Pub. Date: May 5, 2022

(65) Prior Publication Data

US 2023/0405348 A1 Dec. 21, 2023

(30) Foreign Application Priority Data

Oct. 28, 2020 (IT) ........................ 102020000025537

(51) Int. Cl.
*A61N 1/40* (2006.01)
*A61N 1/04* (2006.01)
(Continued)

(52) U.S. Cl.
CPC ............. *A61N 1/40* (2013.01); *A61N 1/0468* (2013.01); *A61N 1/0472* (2013.01); *A61N 1/06* (2013.01); *A61N 1/328* (2013.01)

(58) Field of Classification Search
None
See application file for complete search history.

(56) References Cited

U.S. PATENT DOCUMENTS 6,334,069 B1 * 12/2001 George .................... A61N 1/40 607/2
7,572,985 B2 * 8/2009 George .................... A61N 1/16 174/382
(Continued)

FOREIGN PATENT DOCUMENTS

EP 3488896 A1 5/2019
KR 101290606 B1 7/2013
(Continued)

OTHER PUBLICATIONS

Taizhou Ark International Trade Co., Ltd., "PEEK electrical properties," Jul. 27, 2024, https://www.peekchina.com/blog/peek-electrical-properties.html (Year: 2024).*

*Primary Examiner* — Michael W Kahelin
(74) *Attorney, Agent, or Firm* — Elmore Patent Law Group, P.C.; Joseph C. Zucchero; Carolyn S. Elmore

(57) ABSTRACT

A disposable device designed to enhance the safety of capacitive radiofrequency therapies is described that is able to prevent risks arising from lesions present on the dielectric surface of the insulated electrode or on the stratum corneum of the skin, as well as risks arising from the use of technologies placed on the market before the certification of non-cytotoxicity of the parts applied to the patient (ISO 10993: 2018) was required, as well as the risks of contamination of parts applied in therapies previously performed on other patients.

11 Claims, 6 Drawing Sheets

(51) Int. Cl.
*A61N 1/06* (2006.01)
*A61N 1/32* (2006.01)

(56) References Cited

U.S. PATENT DOCUMENTS

| | | | | |
|---|---|---|---|---|
| 2006/0265034 | A1* | 11/2006 | Aknine | A61B 18/18 607/101 |
| 2010/0233021 | A1* | 9/2010 | Sliwa | A61M 25/0017 422/20 |
| 2014/0249609 | A1* | 9/2014 | Zarsky | A61N 1/40 607/101 |

FOREIGN PATENT DOCUMENTS

| | | | |
|---|---|---|---|
| KR | 20180123894 | A | 11/2018 |
| KR | 20200085450 | A | 7/2020 |

* cited by examiner

A
B
60a
C
60a
D

DISPOSABLE PROTECTION SYSTEM FOR CAPACITIVE RADIOFREQUENCY DELIVERY DEVICES

FIELD OF THE INVENTION

The present invention relates to the field of capacitive radiofrequency delivery devices useful for stimulating skin repair and regeneration.

STATE OF THE ART

Capacitive radiofrequency (RF) is known in the state of the art for its ability to regenerate skin, i.e. to promote the multiplication and reorganisation of the skin layers that have undergone physiological deterioration due to chronoaging or as a result of traumas, wounds and already healed injuries (abrasions, post-surgical scars, acne, burns), as well as to regenerate muscle fibres in sports medicine.

During the 21st century, capacitive radiofrequency has established itself in the field of aesthetic medicine and professional aesthetics, becoming one of the most popular anti-ageing therapies, and in the field of sports medicine, where it is by all means the elective therapy in the aftermath of muscle injuries and tendon inflammation.

It is known that capacitive radiofrequency performs said regenerative action by applying an action similar the that of a capacitor to the skin, and in order to do this, it is necessary to oppose two conductors coated with an insulator. In aesthetic and sports medicine applications, an insulated electrode is used, consisting of an electrical conductor to which the radiofrequency produced by a specific device is transmitted; the electrical conductor is completely coated with an insulating material (plastic, glass, resin, etc.). Such an insulated electrode is applied to the intact skin, where the dermis is characterised by low electrical resistance and therefore acts as a conductor, while the high resistance stratum corneum is the insulator. This coupling thus makes it possible to apply the capacitor concept to the skin, which activates ion exchange in relation to the electrical charge present inside the insulated electrode.

As shown in FIG. 1, the capacitive radiofrequency is based on the capacitor concept; in this case the central conductive core 51 of the insulated electrode 50 and the dermis 54 act as electrical conductors, while the dielectric coating 52 and the stratum corneum 53 act as electrical insulators. The integrity of the electrical insulators 52 and 53 is essential to safely deliver the capacitive radiofrequency. Capacitive radiofrequency has reported, albeit rarely, side effects such as skin burns, potentially due either to chipping of the insulated electrode cover and to injuries to the stratum corneum, furthermore the development of safety standards has also made it compulsory to ensure that the parts applied to the patient, in this case the insulated electrode, are non-cytotoxic, without forgetting the need to ensure maximum hygiene during therapy, a requirement that has become particularly serious since the COVID-19 pandemic.

We know in fact that even the slightest fracture of the surface of the insulator covering the insulated electrode exposes the patient to the risk of a direct radiofrequency discharge. If the integrity of the insulating cover is lost, the delivery is no longer capacitive but resistive and potentially no longer distributed over the surface of the electrode but concentrated in the area of the fracture, which is by all means similar to the action of an electric scalpel, with consequences ranging from intense redness and erythema to skin burns. In FIG. 2 we therefore consider the insulated electrode 50, consisting of a core made of metal or other conductive material 51 (potentially of different sizes, shapes and radii), coated with an insulating material 52 whose surface has a fracture point 55. In this case, the electrical conductor 51 contacts the stratum corneum 53 and determines a radiofrequency discharge 56 directed towards the skin (53, 54), resulting in cautery 57.

Similarly, the safety of the therapy may be compromised by the non-perfect integrity of the stratum corneum. In fact, a lesion in the stratum corneum would determine a localised alteration in the resistance of the insulating layer of the dermis, promoting the concentration of the skin's ionic charges right under such injury, exposing the patient to the risk of a more or less significant burn. We know in fact that electrical charges move according to a well-defined rationale; if there is a negative charge inside the insulated electrode, all the ions with the opposite charge present in the skin, such as Na+ and K+, will tend to be attracted to the electrode, while those with the same charge, such as Cl−, will be moved away, and vice versa if there is a positive electric charge inside the insulated electrode. The attractive force evenly exerted over the entire surface of the intact shielded electrode will be concentrated, by contrast, where the integrity of the stratum corneum is reduced, since the electrical resistance of this area is lower or zero. Therefore, the risk of the concentration of intracutaneous ionic charges being greater than the resistance of the stratum corneum, which is not perfectly intact, is well known and can in some cases injure the stratum corneum itself from the inside, leading to a first-degree burn, which may be followed by a hypotrophic scar. In FIG. 3 we consider the insulated electrode 50, consisting of a conductor 51, temporarily supplied with a negative electric charge, coated with insulating material 52, placed in contact with the stratum corneum 53. On the left-hand side of the drawing we consider an injury in the stratum corneum 58 which reduces its thickness and proportionally its electrical resistance. As a result of this injury, ions with an opposite charge, for example sodium ($Na^+$) and potassium ($K^+$), will be drawn in and tend to concentrate where they find less resistance. This results in the outcome shown in the right-hand side of the drawing, i.e. firstly a burn and then the formation of a hypotrophic scar 59.

Another major risk arising from the application of the capacitive radiofrequency is given by the nature and quality of the insulation used to cover the insulated electrode. A recent edition of ISO 10993 analyses the cytotoxicity risks of the parts applied on the patient, in this case the insulated electrode, and provides higher safety standards than provided in the past (ISO 10993-1:2018 Biological evaluation of medical devices Part 1: Evaluation and testing within a risk management process). The insulating materials normally used to make the external shielding of the insulated electrodes (resin and plastic materials) are generally not certified as non-cytotoxic and could therefore accelerate cell death in the skin they come into contact with, which is exactly the opposite effect of the skin regeneration that capacitive radiofrequency aims to achieve.

If manufacturers of capacitive radiofrequency delivery apparatuses are able to procure ISO 10993-certified material, there still is the risk of using previously marketed insulated electrodes for which a new version of the insulated electrode may not be available due to, for example, models of capacitive radiofrequency generator apparatuses and insulated electrodes that are obsolete and out of production or produced by companies no longer present on the market.

Finally, there is a risk, albeit remote, of contamination of the shielded electrode as a result of application on a previous patient, as the nature of the cover on the shielded electrode prevents it from being sterilised in an autoclave, since both resin and plastic materials would melt. Normal disinfection of the electrode is also not easy because the use of alcohol-based disinfectants is not recommended in these cases; any residues on the surface of the insulated electrode expose the patient to the risk of irreversible sclerosis of the skin capillaries with obvious aesthetic (ectasia, couperose, capillary fragility, etc.) and functional consequences.

In electronics, it is well known that failure of even just one of the two opposite inner insulators of a capacitor, comparable in this case to the insulated electrode cover or stratum corneum, can lead to an internal discharge from one conductor to the other, which can even result in the capacitor blast.

In practice, in medicine too, failure of even just one of the two insulators (dielectric cover of the electrode and stratum corneum) exposes to the same risk of discharge from one conductor to the other, which results in the skin damage described above. It should be noted that the risks reported are rare but known in the scientific literature and that the various publications describe damages occurred to skin tissue without questioning the cause thereof, accepting them as a statistically potential event.

For further confirmation, please note what reported in the user manuals of the capacitive radiofrequency delivery devices:

1. Therapy should not be applied with a shielded electrode that is not perfectly intact;
2. If a shielded electrode is not perfectly intact, it must be replaced with a similar one;
3. Therapy should not be applied to skin tissue that is not perfectly intact.

In practice, the problem of failure of even one of the two insulators is known in the art, but at the moment the only available solution is to scrap the electrodes that are not perfectly intact or not performing the therapy on stratum corneum, even if only partially damaged.

It is therefore currently impossible to apply capacitive radiofrequency to damaged skin tissue, e.g. ulcers, fistulas, sores, etc.

Object of the present invention is to provide a system to improve the safety of capacitive RF delivery devices so as to comply with the requirements of the ISO 10993 standard, to avoid scrapping damaged electrodes, to avoid contamination of the electrode when consecutively applied to different patients and to allow applying capacitive RF on non-intact skin tissue.

Definitions and Abbreviations

RF: radiofrequency

SUMMARY OF THE INVENTION

The present invention solves the aforementioned problems by means of an insulating protective shield made of a non-cytotoxic dielectric material and configured and specifically adapted to be interposed between the insulated electrode of a capacitive RF delivery device and the skin surface of a patient to be treated.

Surprisingly, the shield subject-matter of the invention makes it possible to eliminate the risks arising from capacitive radiofrequency therapies delivered with insulated electrodes that are not perfectly intact and on patients with a non-intact stratum corneum, as well as the risks arising from the adoption of insulated electrodes whose shielding is potentially cytotoxic, i.e. not certified according to the ISO 10993 standard, and the risks of contamination arising from applying the shielded electrode on previously treated patients.

The shield object of the present invention makes it possible to restore the integrity of the insulated electrode and of the stratum corneum, and to guarantee the non-cytotoxicity of the applied part and its absence of contamination arising from therapies performed on previous patients.

Surprisingly, the protective insulating shield of the present invention makes it possible to treat with capacitive RF and thus heal ulcers that cannot be healed with any other type of medical treatment.

In one aspect, the present invention relates to the above-mentioned protective insulating shield for medical use in treating by applying capacitive RF injured and non-intact skin tissues, preferably selected from the group consisting of ulcers, sores, and fistulas.

DETAILED DESCRIPTION OF THE INVENTION

The protective insulating shield of the present invention is preferably disposable.

The protective insulating shield of the present invention may have a thickness of 0.01-20 mm, preferably 0.1-5 mm.

The protective insulating shield of the present invention preferably has a minimum electrical resistance of at least 500 Ohms.

The protective shield can be made in rigid, semi-rigid or flexible form, can be hot-molded or injection-molded, milled or molded in general, and can be made of any dielectric material as long as it is non-cytotoxic, i.e. ISO 10993 certified, preferably PVC or polyoxymethylene (POM; Delrin®), polysulphone (PSU; Udel®), polyphenylsulphone (PPSU; Radel®, Tecason®), polyetheretherketone (PEEK; Ketron®) other non-cytotoxic dielectric material.

Figure 1:
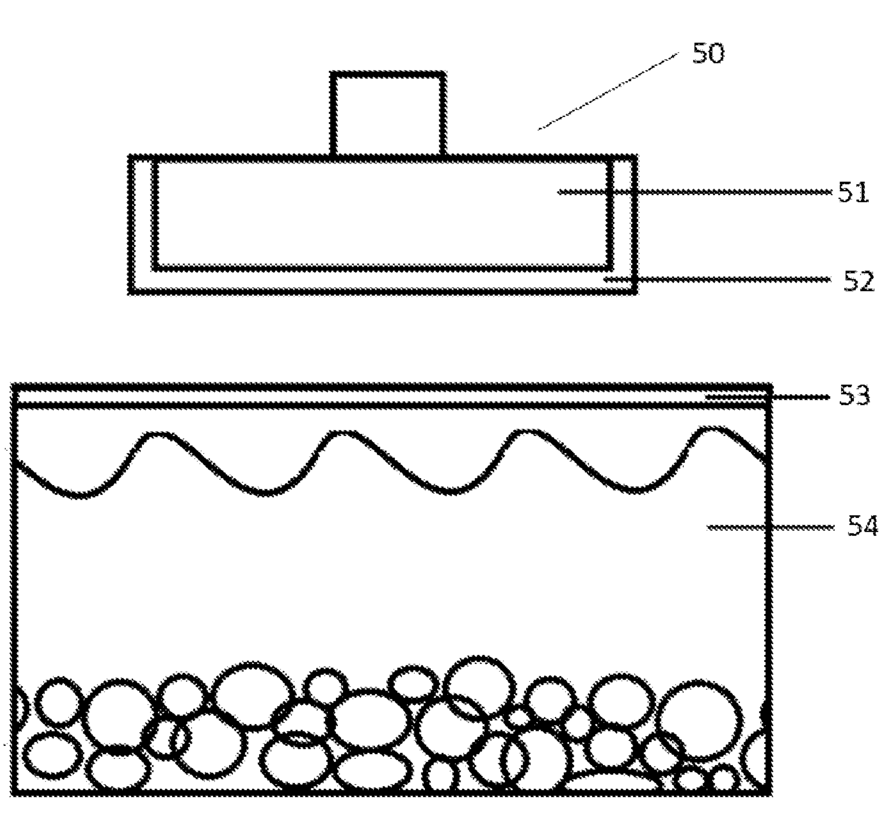
FIG. 1—shows schematically the capacitor between an insulated electrode and the skin of a patient.
Figure 2:
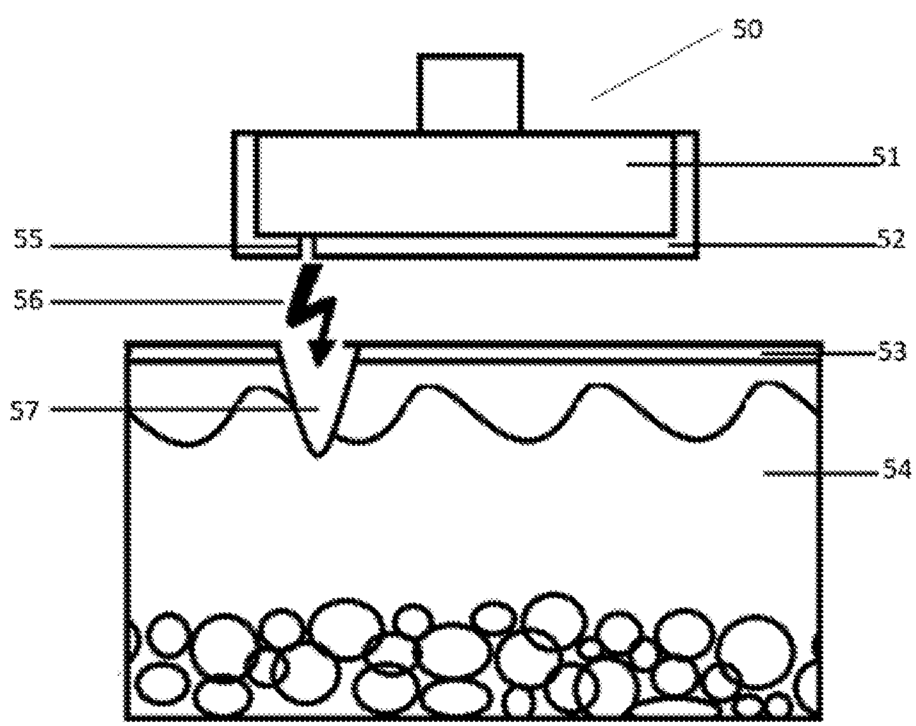
FIG. 2—shows schematically the risks arising from the use of an insulated electrode 50 which is not perfectly intact.
Figure 3:
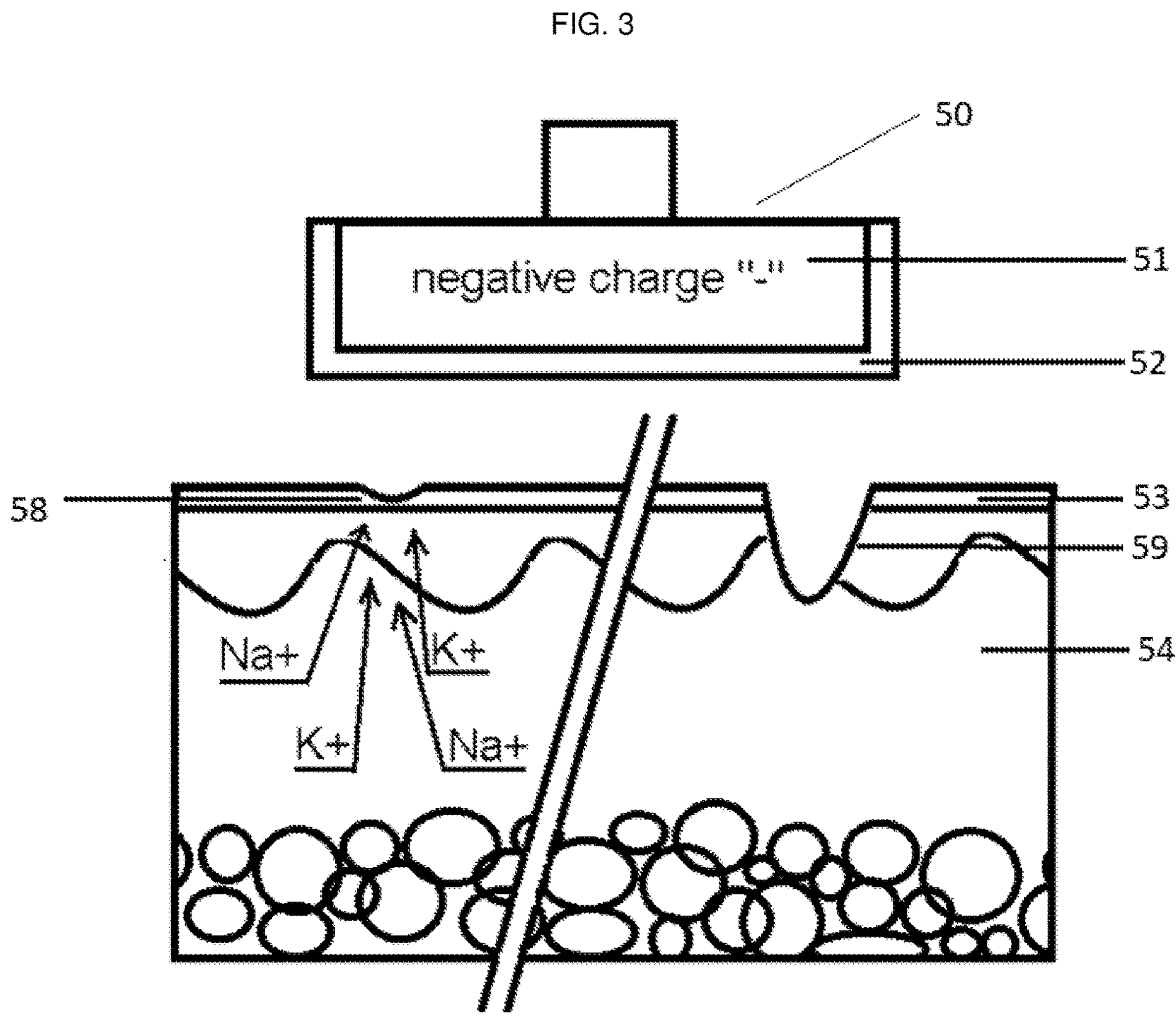
FIG. 3—shows schematically the risks arising from a non-intact stratum corneum.
Figure 4:
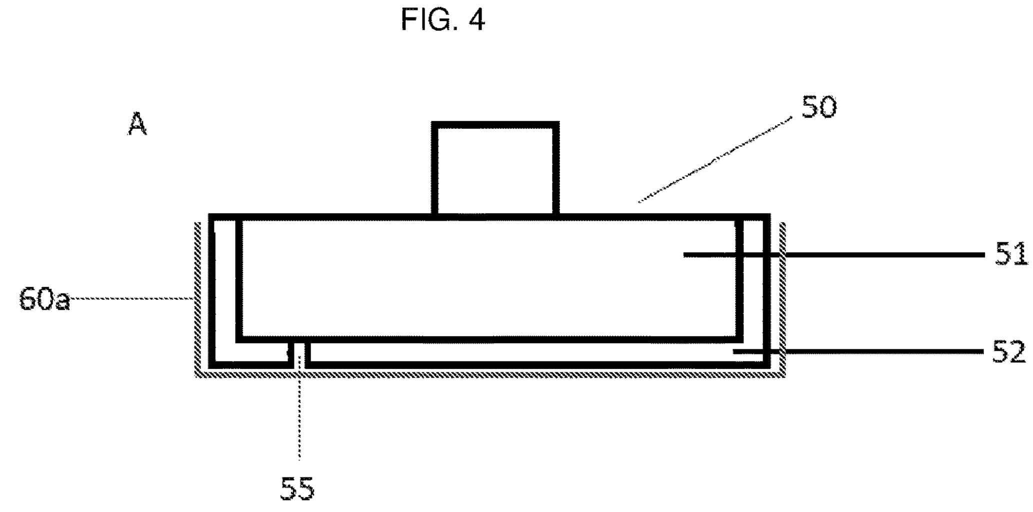
FIG. 4—shows the disposable protective shield according to the present invention in two possible embodiments (A) as a cover cap fitted to the shape of the electrode 50 and (B) as an insulating sheet or membrane.
Figure 4:
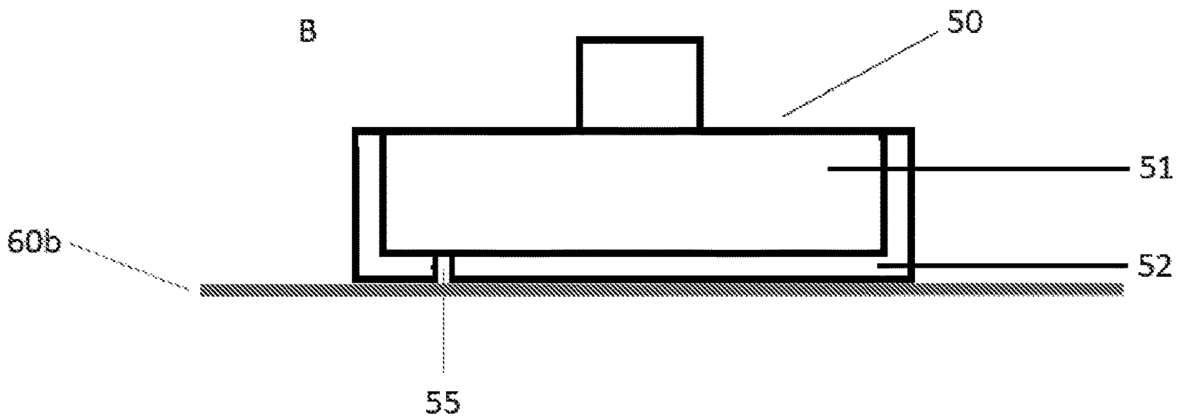

An embodiment of the insulating protective shield of the present invention is in the form of a cover cap 60*a* (FIG. 4A) specifically fitted to the shape of the insulated electrode 50; in this embodiment, the cover 60*a* is hot-molded or injection-molded, milled or otherwise shaped to have a three-dimensional conformation such that it completely envelops the surface of the insulated electrode 50 which is intended to contact the patient's skin.

According to another embodiment, the insulating protective shield may be in the form of a film, membrane or dielectric sheet 60*b* (FIG. 4B) to be applied to the stratum corneum 53 of the patient, in which case the insulated electrode will be slid over said shield 60*b*.

The use of the protective shield of the invention in the application of capacitive RF is compatible with the usual use of electroconductive gel as a gap of electroconductive and lubricating material between the electrode coated with the cap 60*a* and skin or between the skin coated with the membrane 60*b* and the electrode.

Figure 5:
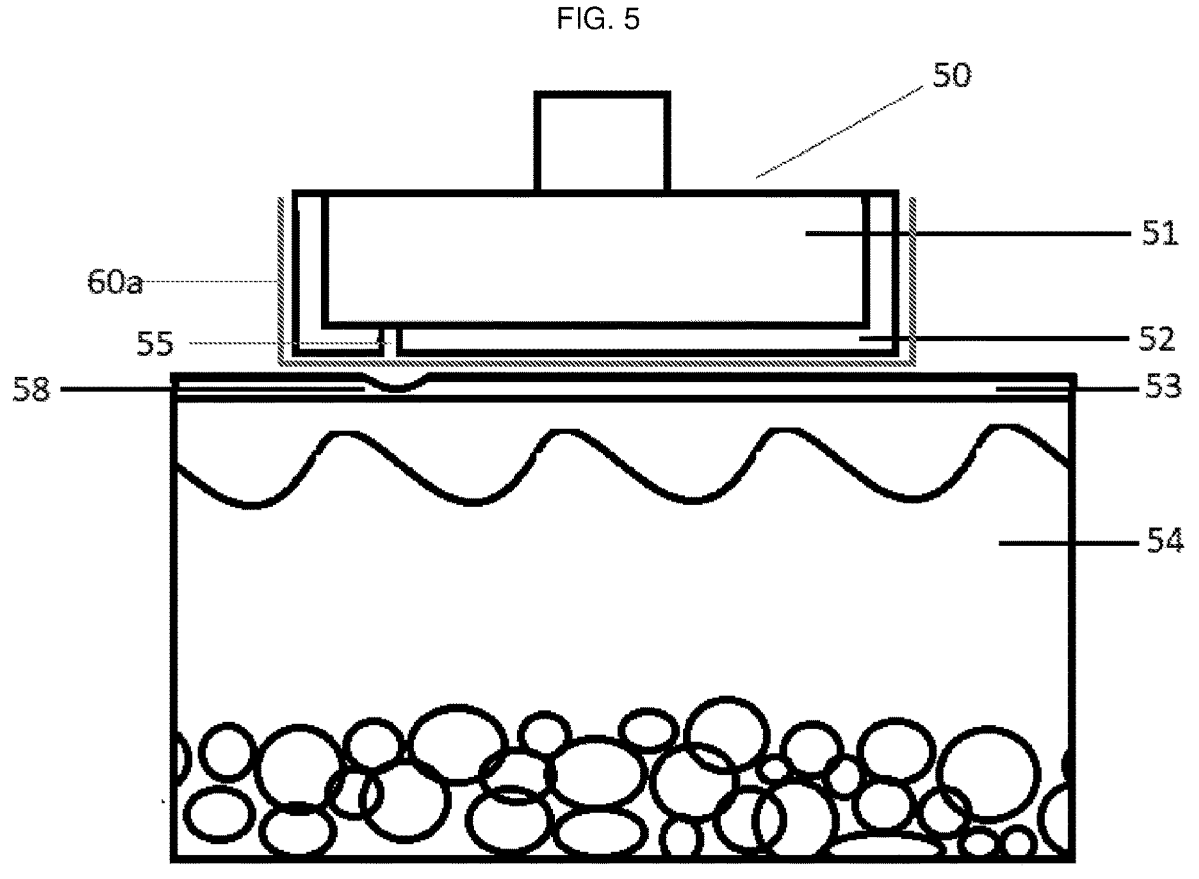
FIG. 5—shows the use of a cover cap 60*a* according to the present invention to cover the insulated electrode 50 and interposed between the electrode 50 and the skin 53 to restore integrity of the insulator 52 and/or the skin 53.
Figure 6:
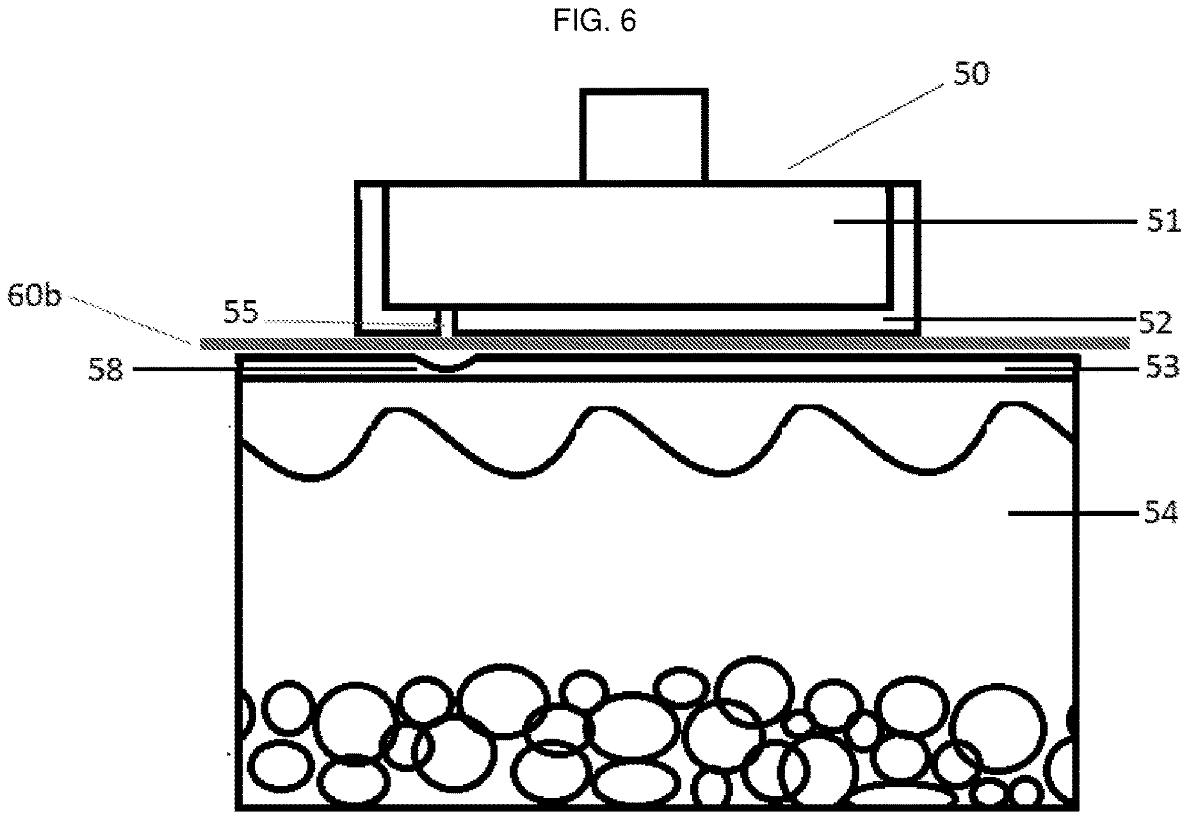
FIG. 6—shows the use of insulating membrane 60*b* according to the present invention in the form of an insulating sheet or membrane and interposed between the electrode 50 and the skin 53 to restore the integrity of the insulator 52 and/or the skin 53.

In FIGS. 5 and 6 it can be appreciated the function of the protective insulating shield 60*a/b* capable of restoring the perfect electrical insulation both in case of fracture 55 of the insulator 52 of the insulated electrode 50, and in case of alteration 58 of the stratum corneum 53, preventing the previously described risks of discharge by the insulated electrode to the skin and the concentration of ionic charges inside the skin.

The insulating shield must be able to interpose itself between the insulated electrode and the patient's skin, thus eliminating both the risks arising from a fracture 55 of the insulating coating 52 and those arising from injuries 58 of the stratum corneum 53, therefore ensuring a perfectly intact and efficient shielding both on the side of the insulated electrode and on the side of the skin, further preventing both the risks related to contamination from previous applications as it is preferably a disposable cover, as well as contact with a potentially cytotoxic shielded electrode, i.e. produced before the new version of ISO 10993.

The protective shield of the present invention can be used in combination with any capacitive RF delivery device for cosmetic or medical purposes. Preferably, for the purposes of the present invention, the capacitive RF delivery device is as described in WO2007/096009 or in WO2019/049105.

In one aspect, the present invention relates to a method for cosmetic treatment, sports medicine treatment or medical treatment of skin lesions to facilitate skin regeneration, said method comprising interposing a protective shield as described above between the insulated electrode of a capacitive RF delivery apparatus and the patient's skin area to be treated.

Preferably, the method of the invention comprises the use of an electrically conductive gel as interspace, in case a protective shield in the form of a cap 60*a* is used, between the cap and the skin of the patient, in the case a protective shield in the form of a film, membrane or dielectric plane 60*b* is used, between the electrode and the shield.

Preferably, the method provides, in case a protective shield in the form of a cap 60*a* is used, sliding the shielded electrode on the skin of the patient in the area to be treated, in case a protective shield in the form of a film, membrane or dielectric plane 60*b* is used, being positioned on the skin of the patient in the area to be treated The present invention can be better understood in the light of the following embodiments.

EXPERIMENTAL PART

Example 1—Cover Cap of an Insulated Electrode

Figure 7:
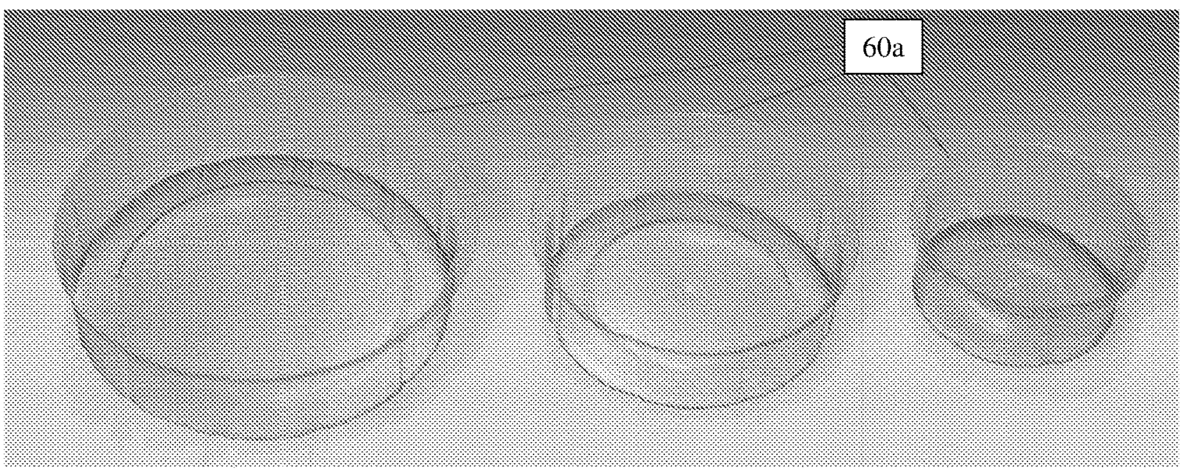
FIG. 7—shows protective caps 60*a* made of PVC according to what described in the example 1.

The protective cap 60*a* can be made of transparent, non-cytotoxic PVC, molded using a mould made of aluminium or other material with an opposite double impression, softened at a temperature ranging from 50 to 200° C. The cap produced has a thickness ranging from 0.3 to 0.5 millimetres, such to allow a significant elasticity thereof to ensure optimum adhesion to the electrode (see FIGS. 6 and 7). Otherwise, the cap could be made of Delrin®, Udel® Polysulfone, Radel®, Ketron®, Tecason® or other non-cytotoxic dielectric material, hollowed out on a lathe or with other mechanical tools or molded. The cap produced has a thickness ranging from 0.3 and 2 millimetres.

Example 2—Protective Film

The protective film 60*b* can be made of transparent, non-cytotoxic PVC, shaped by means of a mould made of aluminium or other material with an opposite double impression, softened at a temperature ranging from 50 to 200° C. The film produced has a thickness ranging from 0.3 to 0.5 mm, such to allow a significant elasticity and flexibility thereof enabling the film to adapt its shape according to the profile of the skin surface, providing stimulation continuity by the shielded electrode to the skin. Otherwise the film could be made of Delrin®, Udel® Polysulfone, Radel®, Ketron®, Tecason® or other non-cytotoxic dielectric material, with a thickness ranging from 0.3 to 2 millimetres, shaped with a mould or other mechanical solution or cut with a laser or milling cutter, with such a stiffness as to allow shaping and flattening the skin surface, which will tend to adhere to the film.

Ulcer Treatment

Figure 8:
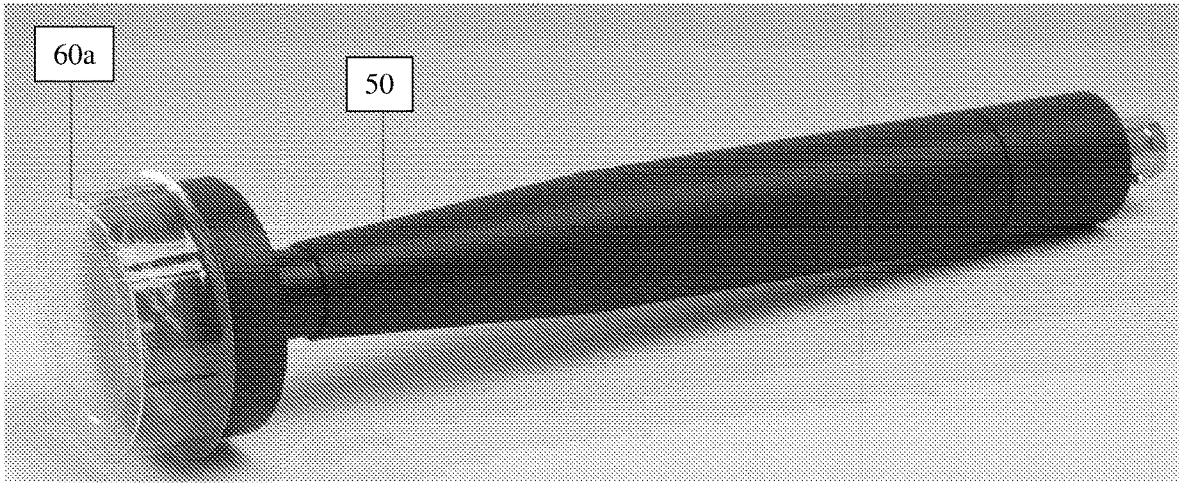
FIG. 8—shows a capacitive electrode 50 provided with a protective cap 60*a* according to the present invention.
Figure 9:
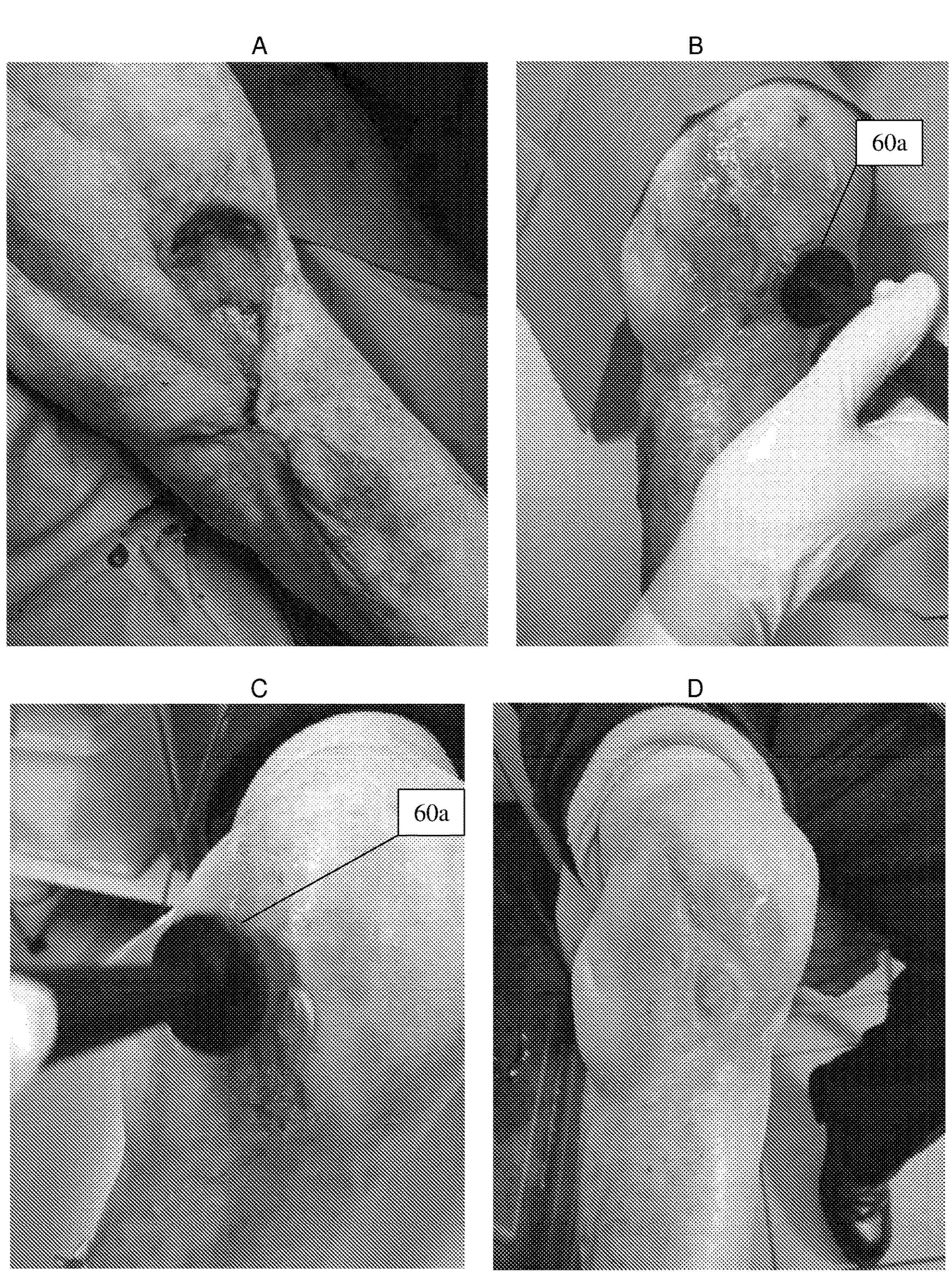
FIG. 9—shows (A) an incurable ulcer, (B and C) application of capacitive RF with an electrode coated with a cover cap 60*a* according to the present invention and (D) the healed ulcer.

The cap of the example 1 has proven to be exceptionally effective in the treatment of ulcers, where it has succeeded in allowing the capacitor effect by artificially restoring the electrical insulation which should have been provided by the intact stratum corneum. The results were greater than any other therapy existing in the state of the art, leading to the correct and complete re-epithelisation of a chronic ulcer (see FIG. 8). The solution provided by the cap to the problem of the lack of integrity of the stratum corneum in case of bedsores, ulcers and fistulas makes it possible to extend the regenerative power typical of capacitive radiofrequencies to these specific fields of application, which were precluded so far.

The ulcer described above had previously undergone all the therapies known in the state of the art without any improvement, but rather continuing to erode, until becoming chronic, for 18 months prior to the treatment carried out with the cap in the example 1.

The invention claimed is:

1. An electrically insulating protective shield for an insulated electrode of a capacitive RF delivery device that must be applied in direct physical contact with the skin surface of a patient to be treated; said insulated electrode comprising a central solid electrically conductive core entirely enclosed within a first insulating dielectric material coating, said insulating protective shield made of non-cytotoxic dielectric material and configured and specifically adapted as a removable dielectric positioned between and in direct physical contact with the first insulating dielectric material coating and the skin surface of the patient to be treated; wherein, when in use, the insulating protective shield forms a second separate dielectric barrier over the first dielectric coating, thereby providing two distinct dielectric layers interposed between the conductive core of the insulated electrode and the skin surface of the patient to be treated.

2. The protective shield according to claim 1, characterized in that the protective shield is disposable.

3. The protective shield according to claim 1, having a thickness of 0.01-20 mm.

4. The protective shield according to claim 1, in rigid, semi-rigid or flexible form.

5. The protective shield according to claim 1, hot-molded or injection-molded, milled or molded.

6. The protective shield according to claim 1, made of PVC or polyoxymethylene (POM), polysulfone (PSU), polyphenylsulfone (PPSU), polyetheretherketone (PEEK).

7. The protective shield according to claim 1, in the form of a cover cap specifically adapted to the shape of an insulated electrode of a capacitive RF delivery device.

8. The protective shield according to claim 1, in the form of a film, membrane or dielectric sheet to be applied on the stratum corneum of the patient.

9. A cosmetic method comprising interposing the protective shield according to claim 1 between the insulated electrode of a capacitive RF delivery device and the patient's skin area to be treated; said insulated electrode consisting of a central solid electrically conductive core entirely enclosed within a first insulating dielectric material coating, wherein the insulating protective shield is placed between and in direct contact with the insulating dielectric material coating of the insulated electrode and the skin surface of a patient to be treated; wherein, during use, the protective shield provides a second separate dielectric barrier forming a double electrical insulation between the conductive core and the patient's skin.

10. A method for the medical treatment of injured or non-intact skin tissues by applying capacitive RF, said method comprising interposing the protective shield according to claim 1 between the insulated electrode of a capacitive RF delivery device and the patient's skin area to be treated; said insulated electrode consisting of a central solid electrically conductive core entirely enclosed within a first insulating dielectric material coating, wherein the insulating protective shield is placed between and in direct contact with the insulating dielectric material coating of the insulated electrode and the skin surface of a patient to be treated; wherein, during use, the protective shield provides a second separate dielectric barrier forming a double electrical insulation between the conductive core and the patient's skin.

11. The protective shield according to claim 3, having a thickness of 0.1-5 mm.

* * * * *